United States Patent [19]

Dombrowski et al.

[11] Patent Number: 4,790,828
[45] Date of Patent: Dec. 13, 1988

[54] SELF-CAPPING NEEDLE ASSEMBLY

[76] Inventors: Mitchell P. Dombrowski, 103 Mapleton, Grosse Point Farms, Mich. 48236; Robert A. Welch, 9573 Winterset Cir., Plymouth, Mich. 48170

[21] Appl. No.: 82,483
[22] Filed: Aug. 7, 1987
[51] Int. Cl.⁴ .............................................. A61M 5/32
[52] U.S. Cl. ................................... 604/198; 604/263; 604/110
[58] Field of Search ............... 604/192, 187, 198, 110, 604/263

[56] References Cited
U.S. PATENT DOCUMENTS
4,735,618  4/1988  Hagen ................................ 604/192

Primary Examiner—John D. Yasko
Attorney, Agent, or Firm—Reising, Ethington, Barnard, Perry & Milton

[57] ABSTRACT

A disposable needle assembly (10,10',10") includes a hub portion (12,12',12") and a hollow needle portion (22,22',22") having a distal tip (26,26',26"). A cap (28,28'28") has a neutral position along the needle portion (22,22',22") proximate to the hub portion (12,12',12") and an extended position for irreversibly capping the distal tip (26,26'26"). A tether (34,34'34") connects the cap (28,28'28") to the hub portion (12,12'12"). The cap (28,28'28") includes a pocket for locking the cap (28,28'28") over the distal tip (26,26'26") when the cap (28,28'28") is in the extended position.

18 Claims, 2 Drawing Sheets

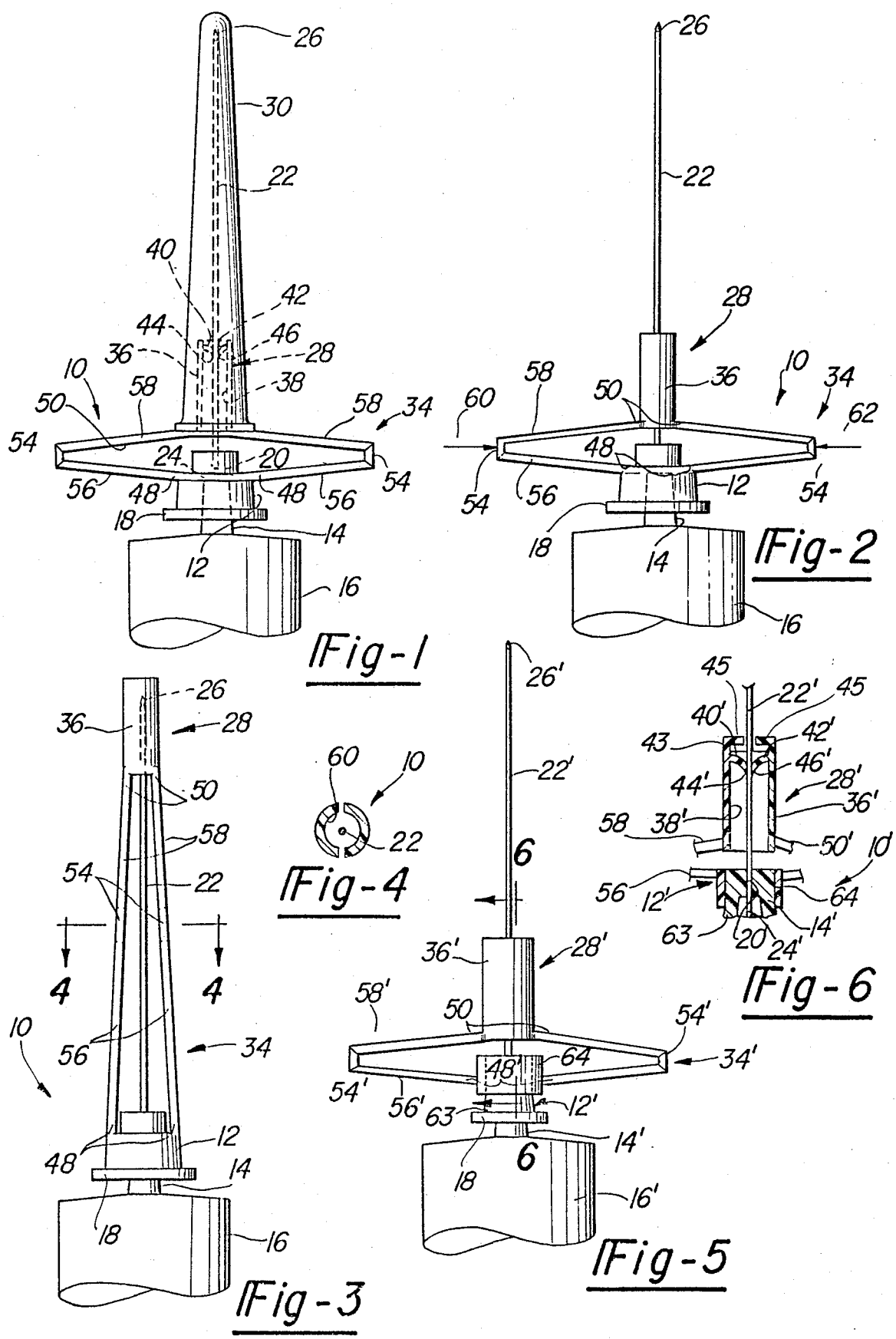

SELF-CAPPING NEEDLE ASSEMBLY

TECHNICAL FIELD

This invention relates generally to hypodermic syringe apparatus, and more specifically relates to a disposable hypodermic needle assembly.

BACKGROUND ART

Health care workers have a continued risk of exposure to infectious agents because of needle stick injuries. Injury can occur during recapping of the needle or from uncapped or improperly stored needles. Health departments are recommending that needles should not be recapped, purposely bent, broken, removed from the disposable syringes or otherwise manipulated by hand in order to avoid accidental puncture injury. It has been further recommended that all needles should be regarded as potentially infective and handled with extraordinary care to prevent accidental injuries. To mitigate the risk of inadvertent puncture, it is recommended that disposable needles should be placed in puncture resistant containers which should be as close as practical to the area in which the needles will be used. However, it is practically impossible to put puncture resistant containers in every patient's room and in every office of a medical facility. Therefore, the needles that have been used must be transported to a puncture resistant container.

The U.S. Pat. Nos. 3,134,380 to Armao, issued May 26, 1964; 3,658,061 to Hall, issued Apr. 25, 1972; and 4,139,009 to Alvarez, issued Feb. 13, 1979, all relate to hypodermic needle assemblies with covers or guards which attempt to shield a used hypodermic needle after use. The Hall patent discloses a catheter needle guard unit including a hub with a cannula needle affixed thereto and a needle guard including a sleeve member with a longitudinal slot adapted to snap over the entire length of the needle. In operation, the needle guard is in the open position when the needle is used to make a venipuncture in a patient and snapped into the closed position manually by a finger of the operator after withdrawal of the needle. The assembly does not totally enclose the needle shaft or the needle tip. The assembly further requires the technician to force the needle guard towards the needle tip allowing for the possibility of either the guard slipping from the technician's grip or the technician missing the needle guard, resulting in accidental puncture. Also, if the needle is bent during use, the sleeve is either prevented from covering the needle or will not contain the entire needle.

The Armao and Alvarez patents both disclose retractable needle guards which extend over the length of the needle assembly prior to use and are retracted as the needle is inserted into the patient. These assemblies require the technician to force the guard to retract as the needle is being inserted. Both guards also do not completely cover the needle tip and can be readily retracted by pressure to the end of the needle guard. Accordingly, accidental puncture can occur merely by the technician accidently depressing the needle guard.

ICU Medical Inc., Huntington Beach, Calif. manufactures a needle marked as "ICU HIGH RISK TM". The assembly includes locking members mounted on the needle shaft and a shield which has a neutral position against the hub and an extended position over the needle tip. The shield is moved from the hub, over the locking member, and locked with the locking member as the shield is moved to the extended position.

The Armao, Alvarez, and ICU Medical, Inc. assemblies all include a shield which cover a significant portion of the needle shaft during use of the needle for an injection. Hence, the assemblies either have less usable needle length if a conventional needle is adapted to the assembly, or the assemblies require a significantly longer needle shaft. Additionally, all these assemblies leave the tip of the needle exposed or capable of being exposed. The tip of the needle is not locked in a completely enclosed guard.

The present invention solves the aforementioned problems by providing a needle guard which does not require a technician to force the needle guard to a retracted position during insertion of the needle, and further essentially irreversibly covers the needle tip. The invention further provides more usable needle length making it adaptable to presently manufactured needle assemblies.

SUMMARY OF INVENTION

In accordance with the present invention, there is provided a disposable needle assembly including a hub portion having a central passageway and a hollow needle portion in fluid communication with the passageway and including a distal tip. Cap means has a neutral position along the needle portion proximate to the hub and an extended position for capping the distal tip. Tether means connects the cap means to the hub portion. The cap means includes at least one flange extending over the distal tip when the cap means is in the extended position and locking means for locking the distal tip under the flange.

FIGURES IN THE DRAWINGS

Other advantages of the present invention will be readily appreciated as the same becomes better understood by reference to the following detailed description when considered in connection with the accompanying drawings wherein:

FIG. 1 is a side elevational view of a preferred embodiment of the present invention mounted on the end of a syringe, a cover being disposed over the needle;

FIG. 2 is a side elevational view of the invention having the protective cover removed;

FIG. 3 is a side elevational view of the invention having the cover thereof in the extended position;

FIG. 4 is a cross sectional view taken substantially along lines 4—4 in FIG. 3;

FIG. 5 is a side elevational view of a second preferred embodiment of the present invention;

FIG. 6 is a fragmentary cross sectional view taken substantially along lines 6—6 of FIG. 5;

DETAILED DESCRIPTION OF THE DRAWINGS

Figure 7:
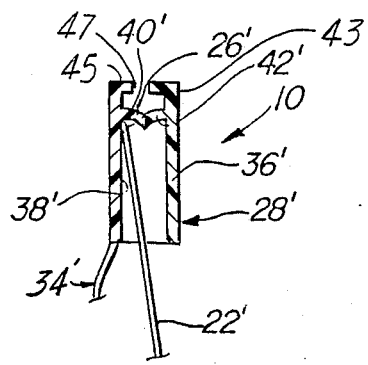
FIG. 7 is a fragmentary cross sectional view of the cover of the present invention extended over a distal tip of a needle.

A first embodiment of a disposable needle assembly constructed in accordance with the present invention is generally shown at 10 in FIGS. 1-4. Primed numerals are used to indicate like or corresponding structure between the several embodiments shown in the remainder of the Figures.

The needle assembly 10 includes a hub portion 12 mounted on a constricted portion 14 of a syringe barrel 16. The hub portion 12 includes a radially outwardly extending flange 18 to secure the hub portion 12 to a syringe with a luer-lock mechanism. Other locking mechanisms can be used to connect the hub portion 12 to the syringe 16.

The hub portion 12 has a central passageway 20. A hollow metallic needle 22 includes a base portion 24 which can be friction fit into the passageway 20. The hollow needle 22 is in fluid communication with the passageway 20. The hollow needle 22 further includes a distal tip 26. The distal tip 26 is a sharp pointed beveled portion of the needle 22 adapted for puncturing the skin.

The assembly 10 includes a cap portion generally indicated at 28. The cap portion 28 has a neutral position shown in FIGS. 1 and 2 wherein the cap portion 28 is positioned adjacent the hub portion 12 thereby exposing the length and distal tip 26 of the needle portion 20. The cap portion 28 also has an extended position as shown in FIG. 3 for capping the distal tip 26 of the needle portion 22.

In FIG. 1, a needle cover 30 is shown mounted on the cap portion 28 and over the entire length of the needle 20. This is the type of cover which would be disposed of prior to use of the needle assembly 10. Reapplication of the cover 30 over the needle 22 exposes the technician of a high risk of stabbing by the distal tip 26 as the open end 32 of the cover 30 must be disposed over the distal tip 26. The cap portion 28 is sized so as to retain the needle cover 30 thereon.

Tether means generally indicated at 34 connects the cap portion 28 to the hub portion 12. The cap portion 28 includes a flange extending over the distal tip 26 and locking means for locking the distal tip under the flange. The locking means and flange are in the form of a pocket, the structure of which will be discussed in further detail below. The pocket contains the distal tip 26 when the cap portion 28 is in the extended position.

The tether means 34 has a neutral condition when the cap portion 28 is proximally located relative to the hub portion 12 and an extended position biasing the pocket onto the distal tip 26 when the cap portion 28 is in the extended position. During use of the assembly 10 to perform an injection, the cap portion 28 and tether means 34 are in the neutral position proximate to the hub portion 12 and apply no resistance to the insertion of the needle portion 22. After use, the cap portion 28 is moved to the extended position, as shown in FIG. 3. In the extended position, the tether 34 is in a stressed condition biasing the cap portion 28 towards the hub 12. In this condition, the tether means biases the pocket over the needle distal tip 26. The tether means in combination with the shape of the pocket locks the cap portion 28 on the distal tip 26.

More specifically, the cap portion 28 includes a substantially cylindrical sleeve portion 36. The sleeve portion 36 includes an inner wall 38. The pocket portion includes the inner surface of a pair of radially inwardly extending flanges 40,42, the flanges 40,42 defining an acute angled shoulder with respect to the adjacent inner wall 38 when viewed in cross section as shown in FIGS. 1 and 6. The angle of the flange 40,42 in combination with the predetermined length of the tether forces the distal tip to be locked within the pocket. The locking means is thereby provided by the combination of the tether means and angled flange 40,42. The flange 40,42 shields and contains the distal tip 26 and the angle of the flange and the tether means locks the distal tip under the flange 40,42 and within the pocket defined thereby.

Each of the flanges 40,42 has a deformable distal edge 44,46 adjacent the distal edge of the other flange. As shown in cross section, the needle portion 22 extends between the distal edges 44,46 by reversibly deforming the distal edges 44,46 when the tether means 34 is in the neutral condition. The distal edges 44,46 perfect a sealed closure with the sleeve 36 about the distal tip 26 when the tether means 34 is in the extended condition.

Unlike prior art assemblies which cover the needle tip but do not completely cap it, the present invention provides a cap which effectively locks the distal tip 26 of the needle 22 therein when the cap portion 28 is moved to the extended position. The tether means 34 effectively biases the cap portion 28 towards the hub portion 12 thereby preventing the cap portion 28 from further extension so as to prevent exposing the distal tip 26 by accidental further extension of the cap portion 28.

This structure effectively prevents further use of the needle assembly. Accordingly post clinical use by drug abusers is discouraged.

The tether means 34 includes at least one flexible arm extending from the hub portion 12 to the cap portion 28, the arm being collapsed or folded in the neutral condition and substantially extended in the extended condition. The tether means 34 includes two end portions 48,50, one of the end portions 48 is integrally connected to the hub portion 12 and the other end portion 50 is integrally connected to the sleeve portion 36.

In the first embodiment shown in FIGS. 1-4, the tether means 34 includes a pair of arms 34, each arm including a midpoint 54 along the length of each arm 34. Each arm 34 includes a rigid portion 56,58 on each side of the midpoint 54. The midpoint 54 is defined by a flexible shoulder 54.

The bevel of the distal tip 26 can be aligned so that the plane of the bevel is parallel to the plane defined by the extent of the arms 34 in the neutral condition, as shown in FIG. 2. The alignment facilitates injection by the arms 34 extend parallel to the surface being punctured thereby not forcing the technician to unnecessarily angle the needle assembly.

In the neutral condition shown in FIGS. 1 and 2, the rigid portions 56,58 are folded at the shoulder 54 to dispose the cap portion 28 adjacent the hub portion 12, the arms 34 being in an unstressed condition. After use of the needle assembly 10, the technician's fingers are used to bias the arms 34 together such that force is applied in the direction of the arrows 60,62 thereby extending the arms 34 along the length of the needle 22 to dispose the cap portion 28 over the distal tip 26. In the extended condition, the arms 34 bias the cap portion 28 towards the hub portion 12 thereby retaining the distal tip 26 within the pocket defined by the inner wall 38 and flanges 40 and 42. (FIG. 7).

As best shown in FIG. 4, each of the arms 34 can include a semicircular surface 61 defining a channel extending along the length of each the arms 34. The channels and the cap portion 28 completely contain the needle 22 when the tether means 34 is in the extended condition. Unlike prior art assemblies which merely cover the distal tip of a needle or a partial length of the needle body, the present invention provides a cover which completely encapsulates the length of the needle 22 and effectively locks the cap portion 28 over the distal tip 26.

FIGS. 5 and 6 show a second preferred embodiment of the present invention generally shown at 10'. In this embodiment, the hub portion 12' includes two portions. A first portion 63 of the hub portion 12' is adapted to be mounted on the constricted portion 14' of the syringe barrel 16'. The first portion 63 of the hub portion 12' can be similar to hub portions presently made for disposable needle assemblies. A collar portion 64 is adhered to the first part 63 of the hub portion 12'. The arms 34' extend from the collar portion 64 to the cap portion 28'.

This embodiment allows the adaptation of previously existing disposable needles to include the present invention. A prior art needle hub 63 is constructed by conventional means and then the collar portion 64 of the present invention is adhered to the the hub portion 63 by conventional means, such as welding, gluing or friction fit.

The cap portion 28 of the present invention is shown in the neutral position in FIG. 6, and in the extended position in FIG. 7. As shown in FIG. 7, the flanges 40',42' effectively lock the distal tip 26' within the cap portion 28'. As the flanges 40',42' are angled downwardly and inwardly, the flanges 40',42' resist outward deflection by the distal tip 26'. Further, the cap portion 28' tends to cant with respect to the length of the needle 28' thereby forcing the distal tip 26' into the shoulder or pocket defined by the acute angled corner between either of the flanges 40',42' and the inner wall 38. As the tether means 34' retains the cap portion 28' over the distal tip 26', the distsl tip 26' is trapped in this shoulder between either of the flanges 40',42' and the inner wall 38' thereby preventing accidental extension of the distal tip 26' through and between the flanges 40',42'. Unlike prior art assemblies, this construction provides a locking mechanism locking the distal tip 26' within the cap portion 28'.

A shield prevents contaminants wiped from the needle 22 onto the flanges 40',42' from being exposed to the technician as shown in FIGS. 6 and 7. The shield includes a tubular portion 43 including a flange 45 extending radially inwardly therefrom to define a central opening 47. The wall about the opening 47 does not contact the needle 26' but is sufficiently closed about the needle 27 to prevent contaminants, such as a drop of blood, from escaping under normal conditions.

Figure 9:
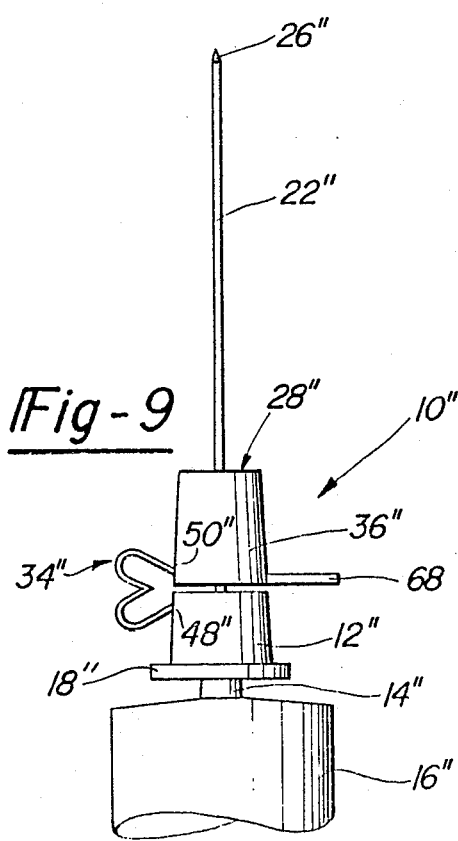
FIG. 9 is a side elevational view of a third preferred embodiment of the present invention having the cover means in the neutral position.
Figure 10:
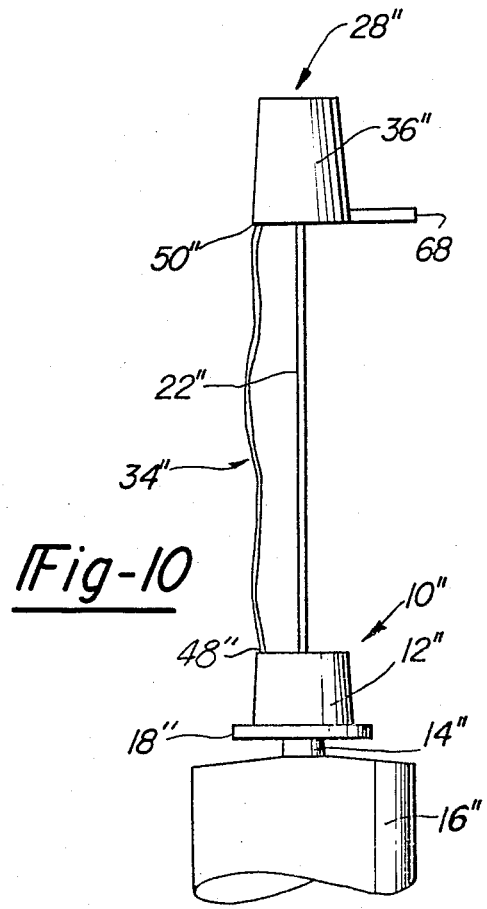
FIG. 10 is a side elevational view of the third embodiment of the present invention with the cover means thereof in the extended position.

A third embodiment of the present invention is shown in FIGS. 9 and 10. A single tether 34" connects the cap portion 28" to the hub portion 12". A tab portion 68 extends radially outwardly from the sleeve portion 36" for providing a handle or grip for the technician to grasp while extending the cap portion 28" over the distal tip 26".

Figure 8:
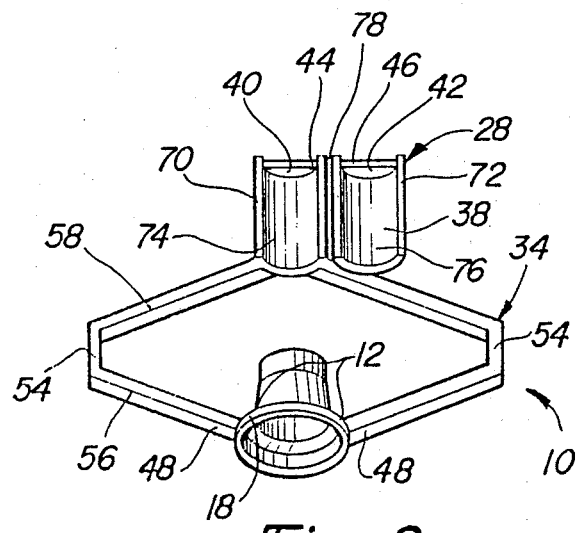
FIG. 8 is an embodiment of the present invention in a preassembled condition.

The present invention further provides a method of making the disposable needle assembly 10, as illustrated in FIG. 8. The hub portion 12 is first molded so as to have a central passageway, a tether 34 extending from the hub 12 and a pair of pre-sleeve halves 70,72, at least one of the halves 70 being connected to each of the tethers 34 at their ends 50. Each of the halves 70,72 include a channel 74,76, respectively. Each of the channels 74,76 have lateral edges and flanges 40,42 extending into the channels 74,76. The pre-sleeve halves 70,72 are connected together along one of the lateral edges 78. The preassembled disposable needle assembly 10 is designed to facilitate manufacturing, such that this assembly may be produced as a single-cavity injection molding. A hollow needle shaft is fitted into the central passageway of the hub portion 12, this step not being shown in the drawing. The beveled needle point 26 is cut in the plane parallel to the arms 54. The length of the needle is aligned with one of the channels 74 of one of the halves 70. The other half 72 is folded over the needle thereby encapsulating the needle proximate to the hub portion 12 within the channels 74,76 of the pre-sleeve halves 70,72. The free lateral edge of the halves 70,72 are adhered together by means common in the art, such as by welding, gluing, or by a snap lock mechanism thereby forming the sleeve 38 about the needle 22 and adjacent the hub portion 12.

As previously discussed and referring to FIGS. 5 and 6, the step of molding the hub 12' may be further defined as first molding the collar portion 64, the collar portion 64 being connected to the pre-sleeve halves 70,72 by the tether 34'. The collar 64 is then adhered to a preformed hub portion 12 by means common in the art, such as by gluing, welding, or snap lock mechanism.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A disposable needle assembly (10,10',10") comprising: a hub portion (12,12'12") having a central passageway (20,20',20"); a hollow needle portion (22,22'22") in fluid communication with said passageway (20,20',22") and including a distal tip (26,26',26"); cap means (28,28'28") having a neutral unstressed position along said needle portion (22,22',22") proximate to said hub (12,12',12") exposing a length of said needle portion (22,22',22") and an extended stressed position wherein said cap means (28,28',28") is biased towards said neutral position for irreversibly capping said distal tip (26,26',26"); and tether means (34,34',34") for connecting said cover means (28,28',28") to said hub portion (12,12',12"), characterized by said cap means (28,28',28") including at least one flange extending over said distal tip (26,26',26") and said cap means (28,28',28") and locking means for locking said distal tip (26,26',26") under said flange (40,40',40",42,42',42").

2. A needle assembly as set forth in claim 1 further characterized by said flange and locking means defining a pocket, said tether means (34,34',34") having a neutral unstressed condition when said cap means (28,28',28") is proximally located relative to said hub portion (12,12',12") and an extended stressed condition biasing said pocket onto said distal tip (26,26',26") when said cap means (28,28',28") is in said extended position.

3. A needle assembly as set forth in claim 2 further characterized by said cap means (28,28',28") including a substantially cylindrical sleeve portion (36,36',36") including an inner wall (38), said locking means including at least one radially inwardly extending portion of said flange (40,40',40",42,42',42") defining an acute angled shoulder with respect to said adjacent inner wall (38,38',38") when viewed in cross section.

4. A needle assembly as set forth in claim 3 further characterized by said cap means (28,28',28") including a pair of radially inwardly extending flanges (40,40',40",42,42',42") each of said flanges (40,40',40",42,42',42"), defining an acute angled pocket with respect to said adjacent inner wall (38,38',38") when viewed in cross section.

5. A disposable needle assembly (10,10',10") comprising: a hub portion (12,12'12") having a central passageway (20,20',20"); a hollow needle portion (22,22',22") in fluid communication with said passageway (20,20',20") and including a distal tip (26,26',26"); cap means (28,28'28") having a neutral unstressed position along said needle portion (22,22',22") proximate to said hub (12,12',12") exposing a length of said needle portion (22,22',22") and an extended stressed position wherein said cap means (28,28',28") is biased towards said neutral position for irreversibly capping said distal tip (26,26',26"); and tether means (34,34',34") for connecting said cover means (28,28',28") to said hub portion (12,12',12"), characterized by said cap means (28,28',28") including at least one flange extending over said distal tip (26,26',26") and said cap means (28,28',28") and locking means for locking said distal tip (26,26',26") under said flange (40,40',40",42,42',42") said flange and locking means defining a pocket, said tether means (34,34',34") having a neutral condition when said cap means (28,28',28") is proximally located relative to said hub portion (12,12'12") and an extended condition biasing said pocket onto said distal tip (26,26',26") when said cap means (28,28',28") is in said extended position, said cap means (28,28',28") including a substantially cylindrical sleeve portion (36,36',36") including an inner wall (38), said locking means including at least one radially inwardly extending portion of said flange (40,40',40",42,42',42") defining an acute angled shoulder with respect to said adjacent inner wall (38,38',38") when viewed in cross section, said cap means (28,28',28") including a pair of radially inwardly extending flanges (40,40',40",42,42',42") each of said flanges (40,40',40",42,42',42"), defining an acute angled pocket with respect to said adjacent inner wall (38,38',38") when viewed in cross section, each of said flanges (40,40',40",42,42',42") having a deformable distal edge (44,44',44",46,46',46") adjacent said distal edge (44,44',44",46,46',46") of said other flange (40,40',40",42,42',42"), said needle portion (22,22',22") extending between said distal edges (44,44',44",46,46',46") by reversibly deforming said distal edges (44,44',44",46,46',46") when said tether means is in said neutral condition and said distal edges (44,44',44",46,46',46") perfecting a sealed unretractable closure with said sleeve (36,36',36") about said distal tip (26,26',26") when said tether means (34,34',34") is in said extended condition.

6. A needle assembly as set forth in claim 2 further characterized by said tether means (34,34',34") including at least one flexible arm extending from said hub portion (12,12',12") to said cap means (28,28',28"), said arm being collapsed in said neutral condition and substantially extended in said extended condition.

7. A needle assembly as set forth in claim 6 further characterized by said tether means (34,34',34") including two end portions (48,48',48",50,50',50"), one of said end portions being integrally connected to said hub portion (12,12',12"), said other end portion (50,50', 50") being integrally connected to said sleeve portion (36,36',36") of said cap means (28,28',28").

8. A needle assembly as set forth in claim 7 further characterized by said tether means (34,34',34") substantially encapsulating said needle portion (22,22',22") when said tether means (34,34',34") is in said extended condition.

9. A needle assembly as set forth in claim 8 further characterized by including a pair of arms, each of said arms (34) including a midpoint (54) along the length of each of said arms (34), each arm (34) including a rigid portion (56,58) on each side of said midpoint (54) and a flexible shoulder (54) at said midpoint, said arms (34) being folded at said shoulder (54) to dispose said cap means (28) adjacent said hub portion (12) in said neutral condition, said arms (34) being extended along the length of said needle (22) disposing said cap means (28) over said distal tip (26), and biasing said cap means (28) towards said hub portion (12) in said extended condition.

10. A needle assembly as set forth in claim 9 further characterized by said arms (34) including an inner surface (60), each of said inner surfaces including a channel extending along the length of each of said arms (34), said channels and said cap means (28) completely containing said needle portion (22) when said tether means (34) is in said extended condition.

11. A needle assembly as set forth in claim 6 further characterized by including a collar portion (64) adhered to said hub portion (12'), said tether means (34') extend from said collar portion (64) to said cap means (28).

12. A needle assembly as set forth in claim 1 further characterized by said cover means including a tab portion (68) extending radially outwardly from said sleeve portion (36") for providing a handle.

13. A needle assembly as set forth in claim 1 further characterized by said cap means (28,28',28") including shielding means over said flange (40,40',40",42,42',42") for shielding and containing any contaminants wiped onto said flange (40,40',40",42,42',42") from said needle portion (22) as said cap means (28,28'28") is moved to said extended position.

14. A needle assembly as set forth in claim 13 further characterized by said shielding means including a cylindrical portion (43) extending from said cap means (28,28',28") beyond said flange (40,40',40",42,42'42") and a shoulder (45) extending radially inwardly from said cylindrical portion (43).

15. A method of making a disposable needle assembly (10) including the steps of: molding a hub portion (12) having a central passageway (20), a tether (34) extending from the hub portion (12), and a pair of pre-sleeve halves (70,72) connected to the tether, each of the halves (70,72) including a channel (74,76) having two lateral edges, at least one of the halves (70,72) having a flange extending into the channel (74,76), the pre-sleeve halves (70,72) being connected together along a lateral edge (78) thereof; fitting a hollow needle into the central passageway; aligning the needle in one of the channels (74) of one of the halves (70); folding the other half (72) over the needle thereby encapsulating the needle (22) proximate to the hub portion (12) within the channels (74,76) of the halves (70,72); and adhering the free lateral edges of the halves (70,72) together thereby forming a sleeve (38) about the needle (22) and against the hub portion (12).

16. A method as set forth in claim 15 further including the step of molding a collar (64) connected to the pre-sleeve (70,72) halves by the tether (34) and adhering the collar (64) to a preformed hub portion (12).

17. A method as set forth in claim 14 wherein the tether including two arms (34) defining a plane, said method further including the steps of beveling the fixed needle (22) is a plane parallel to the plane defined by the arms (34).

18. A disposable needle assembly (10,10',10") comprising: a hub portion (12,12'12") having a central passsgeway (20,20',20"); a hollow needle portion (22,22'22") in fluid communication with said passageway (20,20',20") and including a distal tip (26,26',26"); a cap means (28,28'28") having a neutral unstressed position along said needle portion (22,22',22") proximate to said hub (12,12',12") exposing a length of said needle portion (22,22',22") and an extended stressed position wherein said cap means (28,28',28") is biased towards said neutral position for irreversibly capping said distal tip (26,26',26"); and tether means (34,34',34") for connecting said cover means (28,28',28") to said hub portion (12,12',12"), characterized by said cap means (28,28',28") including at least one flange having a deformable distal edge (40,40',40",42,42',42"), said needle portion (22,22'22") extending against said distal edge (44,44',44",46,46',46") by reversibly deforming said distal edge (44,44',44",46,46',46") when said tether means (34,34'34") is in said neutral condition and said distal edge (44,44',44",46,46',46") perfecting a sealed unretractable closure with said tether means (34,34',34") about said distal tip (26,26',26") when said tether means (34,34',34") is in said extended condition.

* * * * *